United States Patent
Fischer et al.

(10) Patent No.: US 11,357,465 B2
(45) Date of Patent: Jun. 14, 2022

(54) EVALUATING THE RELIABILITY OF A CT VOLUME IMAGE

(71) Applicant: Siemens Healthcare GmbH, Erlangen (DE)

(72) Inventors: Peter Fischer, Erlangen (DE);
Alexander Gemmel, Erlangen (DE);
Gerhard Kleinszig, Forchheim (DE);
Björn Kreher, Bräuningshof (DE);
Holger Kunze, Bubenreuth (DE);
Jessica Magaraggia, Erlangen (DE);
Stefan Schneider, Erlangen (DE);
Markus Weiten, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 47 days.

(21) Appl. No.: 16/598,961

(22) Filed: Oct. 10, 2019

(65) Prior Publication Data
US 2020/0113534 A1 Apr. 16, 2020

(30) Foreign Application Priority Data
Oct. 11, 2018 (EP) .................................... 18199866

(51) Int. Cl.
*A61B 6/00* (2006.01)
*G06T 7/00* (2017.01)
*G06T 11/00* (2006.01)

(52) U.S. Cl.
CPC .......... *A61B 6/5258* (2013.01); *G06T 7/0012* (2013.01); *G06T 11/006* (2013.01);
(Continued)

(58) Field of Classification Search
CPC .......... A61B 6/5258; A61B 6/52; A61B 6/00; G06T 7/0012; G06T 7/0002; G06T 7/00;
(Continued)

(56) References Cited

U.S. PATENT DOCUMENTS

| | | | |
|---|---|---|---|
| 9,269,168 B2 * | 2/2016 | Inglese | A61B 6/5205 |
| 2004/0156561 A1 * | 8/2004 | Yu-Chuan | G06T 3/4076 |
| | | | 382/298 |
| 2018/0182102 A1 * | 6/2018 | Jerebko | G06T 7/0014 |

FOREIGN PATENT DOCUMENTS

| | | | | |
|---|---|---|---|---|
| WO | WO-2004006142 A2 * | 1/2004 | | A61B 5/4064 |
| WO | WO-2012073151 A2 * | 6/2012 | | G06T 11/008 |

OTHER PUBLICATIONS

L. A. Shepp and Y. Vardi, "Maximum Likelihood Reconstruction for Emission Tomography," in IEEE Transactions on Medical Imaging, vol. 1, No. 2, pp. 113-122, Oct. 1982, doi: 10.1109/TMI.1982.4307558 (Year: 1982).*

(Continued)

*Primary Examiner* — Vu Le
*Assistant Examiner* — Courtney Joan Nelson
(74) *Attorney, Agent, or Firm* — Lempia Summerfield Katz LLC

(57) ABSTRACT

Evaluating the reliability of a computed tomography (CT) volume image includes acquiring a first CT volume image and a modified CT volume image that are reconstructed from scanned projection images. From the first CT volume image and the modified CT volume image, digitally reconstructed X-ray images are then calculated. A respective similarity with a corresponding one of the scanned projection images is then determined. Based on a comparison of these similarities with one another, the reliability of the CT volume images is then evaluated.

18 Claims, 2 Drawing Sheets

(52) U.S. Cl.
CPC ............... *G06T 2207/10081* (2013.01); *G06T 2207/20182* (2013.01)

(58) Field of Classification Search
CPC ................... G06T 11/00; G06T 11/003; G06T 2207/10081; G06T 2207/10072; G06T 2207/00
See application file for complete search history.

(56) References Cited

OTHER PUBLICATIONS

C. Studholme, D.L.G. Hill, D.J. Hawkes, Automated 3-D registration of MR and CT images of the head, Medical Image Analysis, vol. 1, Issue 2, 1996, pp. 163-175, ISSN 1361-8415, https://doi.org/10.1016/S1361-8415(96)80011-9. (Year: 1996).*

Dong, Baoyu. "Expectation maximization reconstruction for circular orbit cone-beam CT." International Symposium on Photoelectronic Detection and Imaging 2007: Related Technologies and Applications. vol. 6625. International Society for Optics and Photonics, 2008.

European Search Report for European Patent Application No. 18199866.7-1210 dated Apr. 9, 2019.

Lange, Kenneth, and Jeffrey A. Fessler. "Globally convergent algorithms for maximum a posteriori transmission tomography." IEEE Transactions on Image Processing 4.10 (1995): 1430-1438.

Shepp, Lawrence A., and Yehuda Vardi. "Maximum likelihood reconstruction for emission tomography." IEEE transactions on medical imaging 1.2 (1982): 113-122.

* cited by examiner

EVALUATING THE RELIABILITY OF A CT VOLUME IMAGE

This application claims the benefit of EP 18199866.7, filed on Oct. 11, 2018, which is hereby incorporated by reference in its entirety.

BACKGROUND

The present embodiments relate to evaluating a reliability of a computed tomography (CT) volume image.

Nowadays, CT is a well-established imaging method with which a volume image (e.g., a three-dimensional (3D) image or a 3D image data set) of an examination object (e.g., a patient or a tissue region or suchlike) may be generated. For this purpose, the examination object is transirradiated with X-ray radiation emitted by a radiation source on one side of the examination object and is detected by a detector on the opposite side of the examination object. If a radiation beam used therein has an at least substantially conical or pyramidal form, then this is referred to as a cone beam CT. A plurality of 2D projection images of the examination object is recorded from different angles (e.g., with different angular settings or angulations of the radiation source-detector pair, of the computed tomography unit). The volume image is then reconstructed from these projection images.

Thereby, however, image artifacts may arise such that image quality of the volume image may be impaired and a validity for the respectively relevant examinations may suffer. In order to improve the image quality, for example, methods or processes may be used that automatically carry out modifications or adaptations at least partially based on prior knowledge. For example, this prior knowledge may be taken into account in methods based upon Baysean statistics described by the a priori probability distribution and the maximization of the overall probability. Likewise nowadays, approaches based upon deep learning are also known. Thereby, the prior knowledge for a respective current problem is extracted from a large quantity of annotated training data, for example, in the context of a learning or training process of a neural network. Such approaches have, in many fields, a very good capability for transferring learned information or learned prior knowledge to a respective current problem or result and thus, for example, for improving the image quality of CT volume images. For example, a noise behavior may be improved, a generalization in incompletely reconstructed slice images (e.g., tomosynthesis) may be achieved, or scatter and motion artifacts may be reduced.

However, it may be problematic that a user or observer of a correspondingly reconstructed and, if relevant, modified CT volume image cannot recognize which proportion of the respective volume image is based upon actually scanned, patient-specific data, and which proportion has been derived or modified from the prior knowledge (e.g., does not result directly from the scanned projection images or is not contained therein). This latter proportion derived from the prior knowledge may represent the most probable realization in the context of the prior knowledge. However, in a concrete individual case, it cannot necessarily be assumed that this proportion or the underlying prior knowledge matches the reality of the individual case (e.g., the actual anatomy of the patient). Accordingly, when such image enhancement methods are used for improving the image quality, it may occur that a CT volume image that does not match the real physical anatomy of the patient, at least in details.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a practicability of methods for the automatic improvement of an image quality is increased.

For this purpose, in the present case, a method for evaluating a reliability of computed tomography (CT) volume images or individual features of one or more CT volume images of an examination object is provided. The examination object may be a patient, an organ, or a subregion of the patient, or alternatively, another object accessible to computed tomography. In an act of the method, a computationally reconstructed first CT volume image is acquired from scanned projection images of the examination object. The designation "first CT volume image" serves here merely as a name and does not necessarily relate to a reconstruction or acquisition time point of this CT volume image. The scanned projection images are 2D X-ray images of the examination object that have been recorded from different angles or projection directions. The acquisition of the CT volume image may herein be that the already completely reconstructed first CT volume image is called up, by a system set up to carry out the method or a corresponding data processing device, from a data store or storage medium connected thereto of, for example, a computed tomography system. Similarly, the acquisition may be or include a scanning or recording of the projection images and/or the reconstruction of the first CT volume image. For example, at least one of the scanned projection images may also be acquired (e.g., may be made available to the system or the data processing device for the method for processing or use).

In a further method act of the method according to one or more of the present embodiments, a modified CT volume image of the same examination object created for image artifact reduction by an image enhancement method is acquired. The image enhancement method may be or include, for example, a method mentioned in the introduction and serves for improving an image quality of the first CT volume image or of the modified CT volume image. The first CT volume image and the modified CT volume image thus represent the same or an overlapping volume (e.g., the same or an overlapping region of the examination object, images this). The modified CT volume image may be generated by modification of the reconstructed first CT volume image. As early as during the reconstruction of the first CT volume image, an image enhancement method based, as described in the introduction, upon prior knowledge may be used. This may, in principle, be the same image enhancement method that is also used for the modified CT volume image. However, for example, other parameter values may also be used. Similarly, using the image enhancement method, the modified CT volume image may be generated or reconstructed directly from the scanned projection images (e.g., taking account of prior knowledge regarding the examination object, a respective recording situation and/or the respective reconstruction task). In each case, the modified CT volume image differs from the first CT volume image. For example, at least one variation or alternative of an image enhancement or adaptation that was not used for the first CT volume image may be used for the modified CT volume image. A modification or adaptation may be or include, for example, a continuation of a shape of an anatomical feature beyond a disrupted or unrecorded image region and/or a modification of an intensity or gray value (e.g., at an interference peak). As described for the first CT volume image, the acquisition of the modified CT volume image may be or include a calling up of the modified CT volume image from a data store. Equally, the creation or reconstruction of the modified CT volume image may be part of the method of one or more of the present embodiments.

In a further method act of the method of one or more of the present embodiments, at least one projection direction for which an imaginary or simulated radiation beam extending in this projection direction penetrates at least one voxel of the modified CT volume image is determined. The voxel is modified in comparison with the first CT volume image. In one embodiment, as this projection direction, a projection direction that has been used for the scanning or recording of the projection images, for which, therefore, a scanned projection image of the examination object exists and, for example, has been acquired, may be determined.

In a further method act of the method of one or more of the present embodiments, for the at least one determined projection direction, respectively, at least one digitally reconstructed X-ray image (DRR) is calculated from the first CT volume image and from the modified CT volume image. The digitally reconstructed X-ray image or images calculated or simulated from the first CT volume image and from the modified CT volume image thus show the same or an overlapping region or portion of the examination object from the same viewing direction, and thus, have the same or an overlapping image portion. Based on the manner in which the projection direction used therefore has been determined (e.g., has been selected), at least the one modified voxel passes into the digitally reconstructed X-ray image calculated from the modified CT volume image (e.g., a measure performed by the image enhancement method for improving the image quality). Equally, the corresponding voxel passes without this modification into the digitally reconstructed X-ray image calculated or simulated from the first CT volume image. By this, the digitally reconstructed X-ray images are thus meaningfully comparable with one another.

In a further method act, a similarity is determined between the at least one digitally reconstructed X-ray image calculated from the first CT volume image and the respective corresponding scanned projection image or the corresponding parts of a plurality of the scanned projection images. The corresponding parts of the plurality of the scanned projection images may be the case if the determined projection direction for the DRRs does not correspond to a projection direction that has been used for one of the scanned projection images. In this method act, a similarity is determined between the at least one digitally reconstructed X-ray image calculated from the modified CT volume image and the respective corresponding scanned projection image or the corresponding parts of a plurality of the scanned projection images. In other words, therefore, it is determined or calculated how far or how strongly (e.g., to what extent or degree) the digitally reconstructed X-ray images differ from the corresponding scanned projection image or images. Ideally, a digitally reconstructed X-ray image would correspond to the corresponding scanned projection image (e.g., the scanned projection image recoded in the same projection direction). This is, however, not to be expected in practice as a rule, for example, based on properties of a method or model of the image enhancement method used for reconstructing the CT volume images, assumptions made thereby, and/or a limited calculation accuracy or suchlike. Since, in addition, the first CT volume image and the modified CT volume image differ by definition from one another, it is also to be expected that the digitally reconstructed X-ray images calculated from these CT volume images have different similarities to the corresponding scanned projection image and thus are differently similar or close thereto.

In a further method act of the method of one or more of the present embodiments, for evaluating the reliability of the CT volume images, the determined similarities are compared with one another. At least implicitly, therefore, the reliability of the modifications or changes undertaken by the image enhancement method for the modified CT volume image of the method or model used for the reconstruction of the CT volume images or of an assumption used thereby may similarly be determined or evaluated. Herein, the reliability of the reconstructed first CT volume image and/or of the modified CT volume image may be determined and/or evaluated. If, for example, the similarity between the DRR calculated from the first CT volume image and the corresponding scanned projection image is significantly greater than the similarity between the scanned projection image and the DRR calculated from the modified CT volume image, then this may serve as an indication that the first CT volume image or that the method or model used for reconstructing the first CT volume image from the scanned projection images is relatively reliable. By an inverse argument, this may also provide that the prior knowledge that has explicitly or implicitly been used or taken as a basis for the generation of the modified CT volume image represents or enables, at least for the respective individual case, no reliable description of the respective real examination object. A contradiction may then exist between the prior knowledge and the scan (e.g., the scanned projection images that typically are assumed to be artifact-free).

The reliability of a CT volume image (e.g., a confidence for or in this CT volume image) provides, in the context of the present embodiments, for example, how probable it is that the respectively computationally reconstructed CT volume image corresponds to the reality (e.g., the real physical anatomy of the examination object). The reliability or confidence may be stated for the at least one modified voxel or globally for the respective entire CT volume image (e.g., the entire reconstructed or modified volume or for the reconstruction method used or the image enhancement method used). The reliability may be expressed differently (e.g., as a numerical value, as a percentage, or with a qualitative indication of whether the first CT volume image or the modified CT volume image is more reliable, corresponds with greater probability to the reality). These indications may be derived, for example, directly from a result of a comparison of the determined similarities.

The method of one or more of the present embodiments is independent of the actually used reconstruction or image enhancement methods and may enable an operator or user (e.g., a physician) to decide whether he may solve a particular medical problem or make a diagnosis on the basis of the CT volume images available to him or whether, for example, further examinations are required. Similarly, the user may be supported by the method of one or more of the present embodiments in deciding whether a particular image enhancement method or a particular reconstruction method should be used or not in the particular case. Since the evaluation of the CT volume images using the present embodiments is independent of generation (e.g., independent of the image enhancement and the reconstruction), the present embodiments may serve as an enabler, for example, in the clinical or medical context for many deep learning-based methods developed or currently being developed.

Since with the present embodiments, an evaluation of reliability is available and a simple validation is possible, since the CT volume image reconstructed, for example, in a conventional manner (e.g., without using a deep learning-based method), which may be the first CT volume image or may be different therefrom, may be used as a reference or a fallback possibility, a spread, acceptance, and practical use or usability of reconstruction and/or image enhancement methods on the basis of prior knowledge may be facilitated.

In an embodiment, the first CT volume image is already reconstructed as a CT volume image adapted through estimates based on prior knowledge for an improved image quality. The modified CT volume image is then generated through local modifications from the first CT volume image. In other words, even the first CT volume image contains an estimate that is not necessarily directly contained or recognizable in the scanned projection images. Such an estimate may be, for example, a most probable variant of how a particular feature appears in reality, according to the prior knowledge and in the respective current examination object. For example, an image artifact identified as such or an image field may be replaced by such an estimate, or a recording gap may be filed by such an estimate. That the modified CT volume image has local modifications relative to the first CT volume image provides, for example, that in principle, the same reconstruction or image enhancement method is used for the modified CT volume image as for the first CT volume image. The modified CT volume image and the first CT volume image may thus be, to a significant proportion, identical. The local modifications relate only to one or more subregions of the CT volume images that may amount, for example, to only a few percent of the image volume and may be surrounded by non-modified volume data or subregions.

In an alternative embodiment, for the reconstruction of the first CT volume image, only information contained directly in the scanned projection data and no estimates extending therebeyond may be used, but such estimates may be used for generating the modified CT volume image using the image enhancement method. Herein, the first CT volume image is reconstructed as exactly as possible according to or following the actually scanned data (e.g., the scanned projection images). Herein, a sub-optimum image quality may be accepted in order to be able to use the CT volume image as a reference or comparison value for evaluating the estimates or image enhancements or the prior knowledge.

In an embodiment, the similarities are characterized by a likelihood function. For the evaluation of the reliability, in each case, a likelihood is calculated for the first CT volume and for the modified CT volume using the likelihood function. The likelihood is thus a corresponding function value of the likelihood function. The likelihood for a CT volume image is a maximum if a digitally reconstructed X-ray image calculated therefrom and the corresponding scanned projection image are identical to one another. The likelihood function therefore expresses, in other words, the similarity between simulations and acquired data (e.g., between the DRRs and the corresponding scanned projection image) and evaluates a corresponding error between the simulated or calculated DRRs and the corresponding scanned projection image. The same method or the same process may be used for calculating all the digitally reconstructed X-ray images. The error may then be traced back, for example, to a modification made in the reconstruction of the CT volume images and/or the image enhancement method. A non-normalized likelihood function may be used here. Equally, where available, a normalized likelihood function may be used.

The mechanism or formalism of a likelihood function is sufficiently known as a mathematical method. The use thereof in the present manner according to one or more of the present embodiments with a characteristic or realization of the CT volume images as a varied parameter $\vartheta$ opens up entirely new possibilities for practical medical imaging and the evaluation of diagnoses based thereon. Therefore, as the parameter $\vartheta$ for the likelihood function, a variation of a characteristic or feature or a corresponding realization in the reconstructed CT volume image or images is used. The image or images are modified or varied by the image enhancement method.

Different modifications (e.g., realizations or representations) of the respective feature in the reconstructed CT volume images may be differently probable (e.g., may correspond with different probability to the physical reality of the patient and therefore have different likelihoods in the formalism of the likelihood function). The use of the likelihood function, for example, as the basis for the maximum likelihood method, offers a possibility for determining the reliability in an objective and mathematically-based manner or for evaluating the reliability. Thus, a comparison basis for different reconstruction and image enhancement methods is provided.

In a development, a noise or a noise value $\sigma$ of the at least one scanned projection image is determined. The reliability is then evaluated dependent upon whether a difference between the likelihood $L(\vartheta_{orig})$ calculated for the first CT volume image and the likelihood $L(\vartheta_{mod})$ calculated for the modified CT volume image is larger or smaller than the noise $\sigma$. Thus, through the accessing or use of the noise, depending on the case or situation, different interpretation possibilities suggest themselves for an effect that the modifications brought about by the image enhancement method in the modified CT volume image or corresponding local modifications or adaptations in relation to the first CT volume image possibly already created by the image enhancement method or another image enhancement method have on the likelihood $L(\vartheta_{orig})$ of the first CT volume image, relative to the likelihood $L(\vartheta_{orig})$ of the first CT volume image, or on a likelihood $L(\vartheta_{mod})$ of the modified CT volume image. For the sake of intelligibility, only the complete CT volume images are mentioned, whereby, however, the likelihoods may relate to individual features, image regions, image improvements, or modifications.

If, for example, $$L(\vartheta_{orig}) - L(\vartheta_{mod}) > \sigma$$

applies, then the modification leads to a reduction of the likelihood, and the modified CT volume image thus corresponds with a lower probability to the reality. Accordingly, a respective feature of the first CT volume image is hereby confirmed, since the respective feature of the first CT volume image has a greater likelihood and thus a greater reliability than the modified version, variant, or realization of this feature in the modified CT volume image. In other words, in this case, for example, a local modification or a local change of a realization of an image improvement of the first CT volume image that has been undertaken proceeding from the first CT volume image in order to obtain the modified CT volume image leads to a significant reduction of the likelihood. It may be concluded therefrom that the modification or change (e.g., a changed aspect) is supported by the scanned data. There thus exists a relatively high confidence in the modification or change.

However, if $$L(\vartheta_{mod}) - L(\vartheta_{orig}) > \sigma$$

applies, then the modification by the image enhancement method leads to an increase in the likelihood. The modified CT volume image may then correspond to reality with a greater probability than the first CT volume image. Accordingly, the non-modified feature in the first CT volume image may then be understood or interpreted as contradictory to the scan (e.g., to the scanned projection images). The probability that the reality deviates from the feature in the manner or variant realized in the first CT volume image is therefore relatively high. Thus, by inversion of the argument, the reliability of the first CT volume image is thus relatively low (e.g., lower than the reliability of the modified CT volume image). In other words, in this case, the local modification or change leads to a significant increase in the likelihood. It may be concluded therefrom that the corresponding changed or modified aspect is not supported by the scanned data or is even contradictory thereto. Therefore, a relatively low confidence for the modification or change then results.

In a third case, $$|L(\vartheta_{orig})-L(\vartheta_{mod})| \leq \sigma$$

may apply. In this case, the modification by the image enhancement method leads to no significant change in the likelihood. A respective feature in the first CT volume image or in the modified CT volume image is then therefore not explicitly confirmed by the acquired data (e.g., by the scanned projection images). This may be attributed to the fact that the relevant feature has not been scanned, for example, on use of a tomosynthesis method, or it may provide that the noise σ in the scanned projection image is too great. In other words, it may be concluded in this case that the modification or change is not represented in the scanned data. Therefore, a relatively low confidence (e.g., a confidence close to zero) exists for the modification or change that the changed or adapted aspect is contained in the scanned data (e.g., is supported thereby).

A change in the likelihood is therefore only categorized as significant in the context of the existing change if the change is quantitatively larger than the noise σ of the respective scanned projection image or larger than a variation or uncertainty of the likelihood or the similarity that is anyway to be expected due to the noise σ.

Since the differences described (e.g., the changes in the likelihood) may represent an amount of a local gradient of the likelihood function, methods that are already put to use, for example, in a non-rigid registration may be used. A Markov chain Monte Carlo method may also be used in order to be able to acquire and analyze complex distributions. In other words, these or similar processes or methods may be used, for example, to apply a local modification or adaptation to the first CT volume image that is possibly already improved by the image enhancement method based upon prior knowledge to determine the gradient of the likelihood or the likelihood function.

The use of the noise or the noise value σ described here as a reference or comparison value offers the possibility of undertaking an evaluation or interpretation in a particularly simple manner and inherently adapted to respectively defined conditions in each individual case.

In a further embodiment, for the modified CT volume or CT volume image and/or for the reconstructed first CT volume or CT volume image, a confidence map that shows, at least for each voxel modified by the image enhancement method, a corresponding reliability is generated. In the confidence map, therefore, confidence or reliability values for the modified voxel or voxels or for respective voxels of the first CT volume image that correspond to these voxels (e.g., for each feature shown or reconstructed) are shown or entered. Herein, the confidence map is thus voxel-exact, whereas, however, the overall reliability may equally be given as a global total value for the reconstructed volume (e.g., for the first CT volume image and/or for the modified CT volume image) as a whole. The method described thus enables the confidence map to be created for the respective volume under consideration, independently of the actual image enhancement method. The confidence map may then be made transparent (e.g., output or displayed to the relevant user, a physician or medical practitioner). With this additional information or data, the physician may then decide particularly reliably whether he may answer a particular inquiry based on the first CT volume image or based on the modified CT volume image or not.

Using the confidence map, which may be, for example, overlaid on the respective CT volume image (e.g., switchable on and off), the user may recognize particularly exactly and easily in which image regions of the respective CT volume image a confidence exists in the representation or reconstruction that is sufficient, or too large, or too small for his respective requirements. The pixel-exact or voxel-exact confidence map is advantageous since, using the reconstruction method or the image enhancement method used, in different image regions, different and/or differently intense artifacts or modifications may be introduced or generated. This may be dependent, for example, on local intensity variations (e.g., of a respective local tissue type or tissue composition or suchlike). It may therefore be that in a locally delimited subregion, a modification has been undertaken that leads there to a reduced likelihood, however, that in another local image region, no modification, or a modification that leads there to an increase in the likelihood, has been made. Depending thereon which image region is relevant in the respective individual case, for example, for a diagnosis, using the confidence map, an optimum selection of the CT volume image to be used may then be made particularly easily and reliably.

In a development, the reliabilities or confidence values entered in the confidence map are color-coded according to a pre-defined scheme depending upon sizes or values. Thereby, a pre-defined absolute or relative scale may be used or taken as a basis. In other words, therefore, the confidence map is generated as a heat map. This may enable a particularly easy, fast, and intuitively graspable interpretation of the confidence map, including for inexperienced or untrained personnel.

In a further embodiment, an indication or a warning may be issued automatically to a user if the reliability is smaller than a pre-determined threshold value. By this, an increased level of ease of use may be achieved since in the case of a reliability lying above the pre-determined threshold value, for example, no further measures or input by the user are needed or must be requested. However, in the event that the reliability is lower than the pre-determined threshold value, by the automatically issued indication or the automatically output warning, the probability that the respective operator or user makes a decision that is critical from a medical standpoint based on a correspondingly less reliable CT volume image, for example, without the correspondingly low reliability being known to him, is reliably reduced. The indication or the warning may be generated and output, for example, automatically by a system established and used for carrying out the method of one or more of the present embodiments. For this purpose, the system can include a data processing device for processing the scanned projection images and/or the first CT volume image and may itself have a data store in which different reconstruction or image enhancement methods (e.g., corresponding programs or program modules) are stored. By the automatic selection and/or use of the alternative method or methods as the alternative reconstruction or image enhancement method, an improved convenience of operation or use for a respective user may be achieved.

A further aspect of the present embodiments is a computer program or a computer program product that includes commands or instructions that, on execution of the computer program by a computer, cause the computer to carry out at least one embodiment of the method (e.g., automatically or semi-automatically). The computer may be, for example, the system mentioned in relation to the method of one or more of the present embodiments, or a part of this system. The computer program thus codes or represents, in other words, the method acts of at least one embodiment of the method. The computer program may be configured and arranged, for example, for loading into an electronic or electronically readable or computer-readable data store of the computer (e.g., a data processing device of a computed tomography system).

A further aspect of the present embodiments is a data carrier signal that transmits or may transmit at least one embodiment of the computer program.

A further aspect of the present invention is a computer-readable storage medium (e.g., a non-transitory computer-readable storage medium) that is a computer-readable data carrier on which at least one embodiment of the computer program or computer program product is stored. The computer-readable storage medium may thus be, for example, a data carrier for the aforementioned computer, the aforementioned data processing device, the aforementioned system, or the aforementioned computed tomography system. Further commands or control instructions for the computer, the data processing device, the system, or the computed tomography system may be stored on the computer-readable storage medium or the data carrier. These may be configured and arranged, for example, to generate one or more queries to a user or operator, to acquire corresponding user input and/or, for example, to generate the aforementioned indication or the aforementioned warning.

A further aspect of the present embodiments is a system for evaluating a reliability of CT volume images of an examination object. The system includes an acquisition device for acquiring a computationally reconstructed first CT volume image from scanned projection images of the examination object. The acquisition device may equally be configured for acquiring a modified CT volume image of the same examination object generated for image artifact reduction by an image enhancement method. The acquisition device may herein be part of a data processing device. Equally, the acquisition device may be or include a recording device of a computed tomography system for recording (e.g., for scanning) the scanned projection images. The acquisition device may thus include, for example, the aforementioned detector and the aforementioned radiation source.

The system includes a data processing device connected to the acquisition device, which includes at least one embodiment of the computer-readable storage medium and is configured for carrying out the computer program stored thereon. In other words, the system is thus configured for carrying out or executing at least one variant of the method. Accordingly, the system may include at least a selection of the properties and/or parts or components mentioned in relation to the other aspects of the present embodiments (e.g., in relation to the method, the computer program, and/or the computer-readable storage medium). This may relate, for example, to an output device for outputting the aforementioned indication or the aforementioned warning or a user interface for receiving or acquiring user input or suchlike.

For carrying out the computer program, the data processing device of the system may have, for example, a microprocessor, a microchip or a microcontroller that is connected to the computer-readable storage medium.

The system may be a computed tomography system. Equally, the system may be, for example, a computer or a computer device that may be connected, for example, to a remotely arranged computed tomography system. The system (e.g., the data processing device of the system) may thus be part of a computed tomography system, but equally, for example, may be arranged in another room on-premise, remotely in a computer center, or, for example, may be realized as a Cloud server.

The properties and developments of the method, the computer program, and the computer-readable storage medium, and also the corresponding advantages set out above and in the following are each analogously and reciprocally transferable between these aspects of the present embodiments. Such developments of the aspects that have embodiments that, for the avoidance of unnecessary redundancy, are not explicitly described here in the respective combination or are not separately described for each aspect of the present embodiments, thus also belong to the invention.

DETAILED DESCRIPTION

Figure 1:
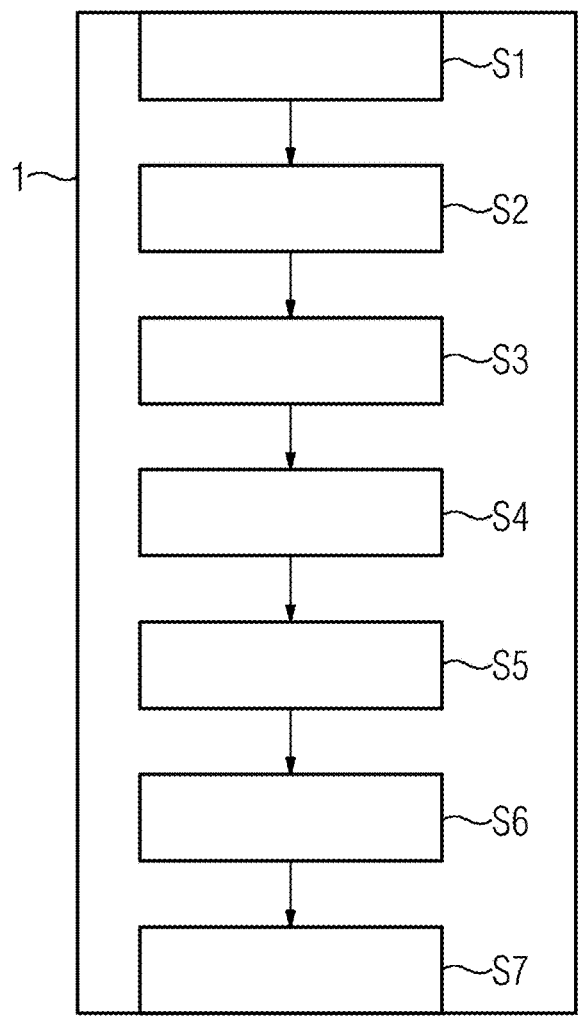
FIG. 1 shows a schematic representation of one embodiment of a computer-readable storage medium with schematically indicated program modules for a method for evaluating a reliability of a CT volume image.

The embodiments set out in the following are exemplary embodiments of the invention. The components of the embodiments, as described in the exemplary embodiments, each represent individual features and are also to be considered independently of one another. The components of the embodiments also further develop the invention independently of one another and are thus also to be considered individually or in a different combination from that shown. The embodiments described are also enhanceable through others of the previously described features of the invention.

In the drawings, details having the same function or corresponding to one another are provided with the same reference signs.

In computed tomography (CT), for artifact reduction and image enhancement, methods that use prior knowledge (e.g., in the form of an a priori distribution or trained neural networks) are employed. These methods have conventionally tended to be used conservatively (e.g., with restraint). One reason for this is that the prior knowledge mostly relates to healthy people and not, for example, to pathologies or fractures, since these may manifest in a wide variety of ways. In addition, with deep learning-based methods, it is barely predictable whether pathologies or fractures will actually function correctly in real situations (e.g., if the corresponding situations were not trained in during a training phase). It may thus be problematic that a systematic determination of equivalence classes in a black box test is not possible.

FIG. 1 shows schematically a computer-readable storage medium 1 (e.g., a non-transitory computer-readable storage medium) with a series of blocks S1 to S7 that represent method acts of a method for evaluating a reliability of CT volume images of an examination object (e.g., in the present case, a patient) or corresponding program modules of a computer program or a computer program product implementing this method. The method set out here or the corresponding computer program thus serves for quantifying a reliability or confidence of particular features of a CT volume image that represents or depicts a real volume of the examination object.

In the method act or block S1, for this purpose, two-dimensional projection images of the examination object are acquired by a computed tomography unit or a computed tomography system.

In a method act or block S2, from these projection images, a first CT volume image is reconstructed (e.g., a three-dimensional data set that represents the examination object is created). Thereby, depending on the application case, an image enhancement on the basis of prior knowledge may be used.

In a method act or block S3, by an automatic image enhancement method, an image enhancement or image correction of the first CT volume image is carried out, and thereby, a modified CT volume image is generated. This may involve, for example, local modifications or realization variants for aspects (e.g., details) of the first CT volume image.

In a method act or block S4, from the first CT volume image and from the modified CT volume image, digitally reconstructed X-ray images are generated (e.g., simulated or calculated).

Both a digitally reconstructed X-ray image calculated from the first CT volume image and also a digitally reconstructed X-ray image calculated from the modified CT volume image may differ from the scanned projection image recorded in the corresponding projection direction. The CT volume images may thus have artifacts or image interference. These may result therefrom when a model used for reconstructing the respective CT volume image does not match the reality in an individual case (e.g., in some aspects or assumptions, the real physical anatomy or the real physical properties of the respective examination object) and/or does not match a recording method of the scanned projection images that is used or a property of the computed tomography unit or the X-ray radiation used. Examples of this may be, for example, beam hardening or a movement of the examination object during the recording of the scanned projection images or suchlike.

In a method act or block S5, using a likelihood function, a likelihood for the first CT volume image and a likelihood for the modified CT volume image are calculated taking account of the similarities of the digitally reconstructed X-ray image to the corresponding scanned projection image or images. Thereby, a likelihood gradient (e.g., a gradient of the likelihood function) is calculated.

A difference of these calculated likelihoods is compared with or put into relation to a noise or noise value σ of the respective scanned projection image. Thereby, different configurations are possible, of which some are illustrated by way of example in FIG. 2, FIG. 3, and FIG. 4. Therein, an exemplary progression of the likelihood function is plotted in each case. On an x-axis or abscissa 2, in each case, a parameter $\vartheta$ that expresses different characteristics of the reconstructed volume (e.g., different variations or realizations of a feature modified by the image enhancement method. $\vartheta_{orig}$ corresponds thereby to the realization in the first CT volume image) is entered. $\vartheta+$ and $\vartheta-$ correspond to different possible realizations of the respectively observed feature in the modified CT volume image or in different modified CT volume images. On a y-axis or ordinate 3, the likelihood L is entered in each case.

Figure 2:
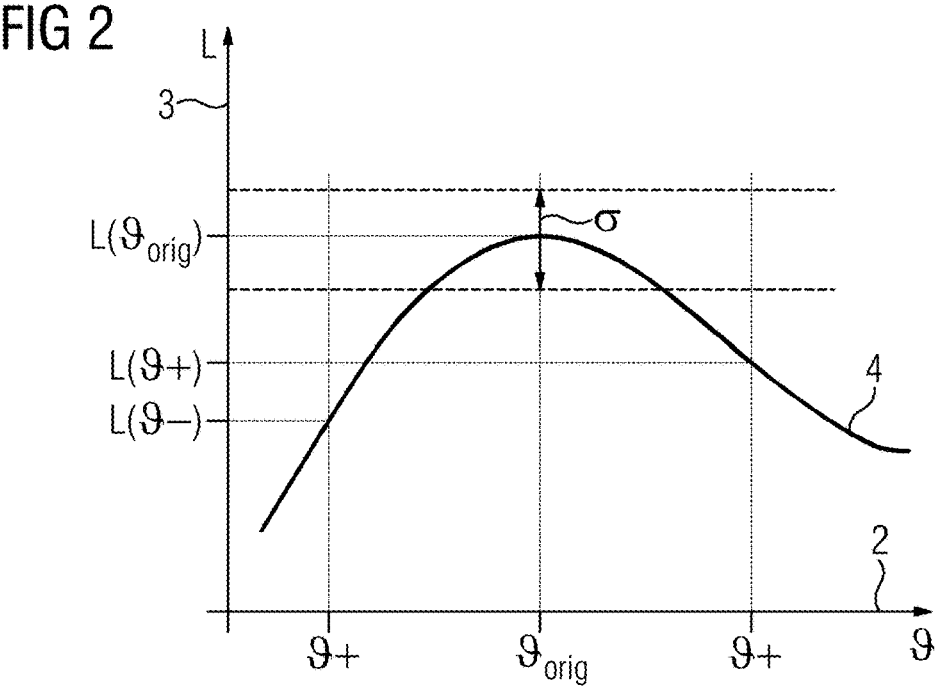
FIG. 2 shows a graphical illustration of a first example of a progression of a likelihood function.

In the first progression 4 of the likelihood function shown in FIG. 2, the likelihood L rises from a value $L(\vartheta-)$ to a value $L(\vartheta_{orig})$ and then falls off again to a value $L(\vartheta+)$. $L(\vartheta-)$ and $L(\vartheta+)$ correspond to the likelihoods of different modified CT volume images and may also be designated $L(\vartheta_{mod})$. Since the first CT volume image has been generated directly from the scanned projection images without the image enhancements used for the modified CT volume, a size of the noise value σ of the scanned projection images or a variation or uncertainty to be expected in the likelihood L due to noise is also shown as $\vartheta_{orig}$. In the first progression 4 shown in FIG. 2, both for $\vartheta-$ and also for $\vartheta+$ (e.g., grouped together for $\vartheta_{mod}$), the following inequality applies $$L(\vartheta_{orig})-L(\vartheta_{mod})>\sigma.$$

This provides or is interpreted to be that the respectively observed feature in the reconstructed first CT volume image is confirmed by the scan (e.g., the scanned projection images and the modifications or realizations $\vartheta-$, $\vartheta+$ of this feature undertaken for the modified CT volume images have a smaller likelihood L, correspond with a lower probability to reality).

Figure 3:
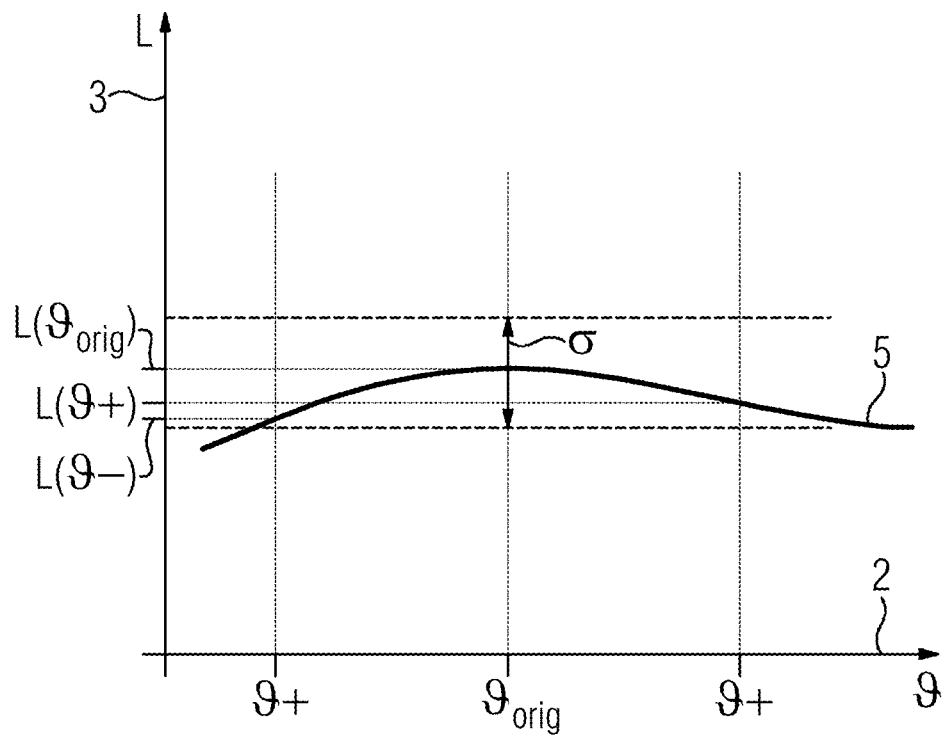
FIG. 3 shows a graphical illustration of a second example of a progression of a likelihood function.

A second progression 5 of the likelihood function shown in FIG. 3 has, in comparison with the first progression 4, a smaller curvature or gradient. In this case, the changes of the likelihood for the modified CT volume images brought about by the modifications as compared with the likelihood of the first CT image or the realization contained therein of the respective observed feature is lower than the noise value σ. Accordingly, the following inequality applies $$|L(\vartheta_{orig})-L(\vartheta_{mod})|\leq\sigma.$$

The modifications of the feature or the realization $\vartheta$ of the observed feature thus leads to no significant change in the likelihood. This provides or is interpreted to be that no significance for the observed feature may be found in the scan (e.g., in the scanned projection images).

Figure 4:
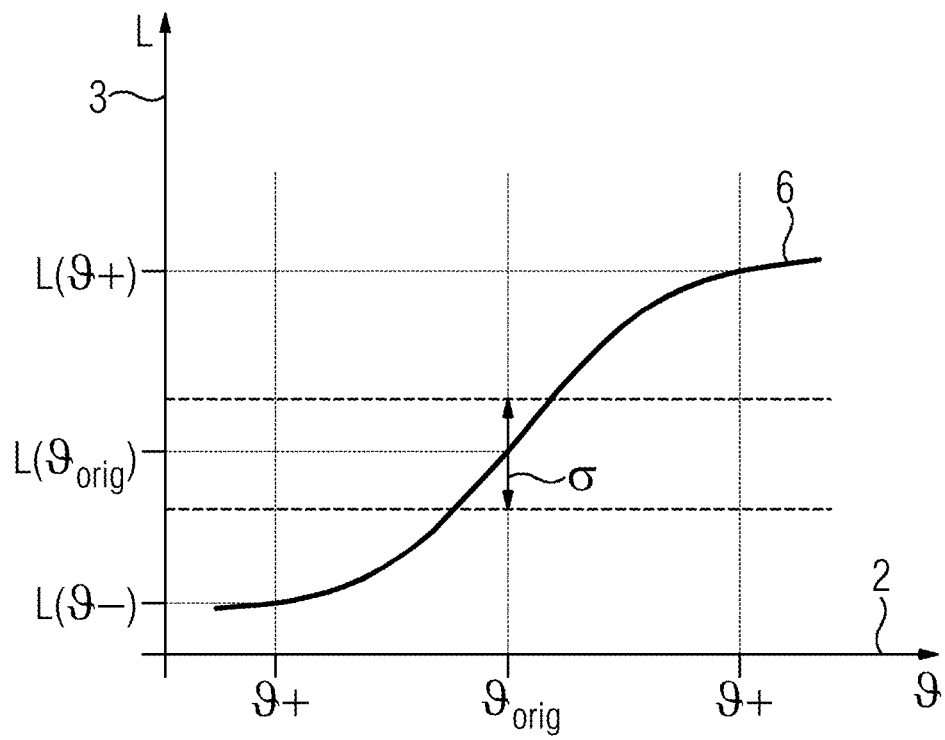
FIG. 4 shows a graphical illustration of a third example of a progression of a likelihood function.

FIG. 4 shows a third progression 6 of the likelihood function. Herein, the likelihood increases from the value $L(\vartheta-)$ for a first modified realization $\vartheta-$ of the observed feature to a value $L(\vartheta_{orig})$ for the realization $\vartheta_{orig}$ in the first CT volume image, and further to a value $L(\vartheta+)$ for a second realization $\vartheta+$ in a second modified CT volume image. Thereby, the likelihood $L(\vartheta+)$ for the second realization $\vartheta+$ is thus greater than the likelihood $L(\vartheta_{orig})$ for the realization $\vartheta$ of the first CT volume image, so that for the second modified realization $\vartheta+$, the inequality $$L(\vartheta+)-L(\vartheta_{orig})>\sigma$$

applies. The second change or modification (e.g., the realization $\vartheta+$) thus leads to an increase or a rise in the likelihood L for the correspondingly modified CT volume image as compared with the first CT volume image. This provides or is interpreted to be that the scan (e.g., the scanned projection images) contradicts the reconstructed first CT volume image or the realization $\vartheta_{orig}$ of the observed feature provided therein. Accordingly, the second modified CT volume image with the realization $\vartheta+$ may then be used as the basis, for example, for an evaluation or diagnosis.

In a corresponding manner, the likelihoods L for each modified feature (e.g., for a plurality of modified voxels of the CT volume images) may be calculated and compared with one another.

In a method act or block S6, based on the determined likelihood, a confidence map and/or a global confidence value or reliability value is generated or determined. The confidence map or the confidence value or reliability value may then be displayed to a user as an indication and/or used as a deciding criterion in order to determine, for example, automatically or semi-automatically, whether an image enhancement method used or usable for the generation of the modified CT volume image or images should or should not be offered or used.

In a method act or block S7, a comparison of the determined likelihood(s), confidence value(s), or reliability value(s) may be carried out automatically with a corresponding pre-determined threshold value. It is thereby established that the pre-determined threshold value is undershot, and so, a corresponding indication or a corresponding warning may be generated automatically and output to a respective user.

As a whole, the examples described show how a practicability of a method for automatically improving an image quality may advantageously be improved.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for evaluating a reliability of computed tomography (CT) volume images of an examination object, the method comprising:
   acquiring a computationally reconstructed first CT volume image from scanned projection images of the examination object;
   acquiring a modified CT volume image of the examination object for image artifact reduction using an image enhancement method, the image enhancement method using a first image enhancement type;
   determining at least one projection direction for which a simulated radiation beam penetrates at least one voxel of the modified CT volume image, the at least one voxel being modified in comparison with the computationally reconstructed first CT volume image;
   calculating, for the at least one determined projection direction, at least one digitally reconstructed X-ray image, respectively, from the computationally reconstructed first CT volume image and from the modified CT volume image;
   determining a similarity, in each case, between the at least one digitally reconstructed X-ray image calculated from the computationally reconstructed first CT volume image and the respective corresponding scanned projection image, and between the at least one digitally reconstructed X-ray image calculated from the modified CT volume image and the respective corresponding scanned projection image;
   comparing, for evaluating the reliability of the CT volume images, the determined similarities with one another; and
   automatically using or proposing a method for image optimization different than the image enhancement method when the reliability of the modified CT volume image is smaller than a pre-determined threshold value, the method for image optimization using a second image enhancement type, the second image enhancement type being different than the first image enhancement type.

2. The method of claim 1, wherein the computationally reconstructed first CT volume image is already reconstructed as a CT volume image adapted through estimates based on prior knowledge for an improved image quality, and the modified CT volume image is generated by local modifications from the computationally reconstructed first CT volume image.

3. The method of claim 1, wherein acquiring the computationally reconstructed first CT volume image comprises reconstructing the computationally reconstructed first CT volume image using only information contained directly in the scanned projection images and no estimates extending therebeyond, and
   wherein acquiring the modified CT volume image comprises generating the modified CT volume image using the estimates.

4. The method of claim 1, wherein the determined similarities are characterized by a likelihood function,
   wherein the method further comprises calculating, for evaluation of the reliability using the likelihood function, in each case, a likelihood for the computationally reconstructed first CT volume and a likelihood for the modified CT volume, and
   wherein the likelihood for a CT volume image is a maximum when a digitally reconstructed X-ray image calculated therefrom and the corresponding scanned projection image are identical.

5. The method of claim 4, further comprising:
   determining a noise of the scanned projection image; and
   evaluating the reliability depending on whether a difference between the likelihood calculated for the computationally reconstructed first CT volume image and the likelihood calculated for the modified CT volume image is larger or smaller than the determined noise.

6. The method of claim 1, further comprising generating, for the modified CT volume image, the computationally reconstructed first CT volume image, or the modified CT volume image and the computationally reconstructed first CT volume image, a confidence map that shows at least for each voxel modified by the image enhancement method, a corresponding reliability.

7. The method of claim 6, wherein the reliabilities entered in the confidence map are color-coded according to a pre-defined scheme depending upon sizes.

8. The method of claim 1, further comprising automatically issuing an indication to a user when the reliability is smaller than a pre-determined threshold value.

9. The method of claim 1, wherein automatically using or proposing the method for image optimization using the second image enhancement type when the reliability of the modified CT volume image is smaller than the pre-determined threshold value comprises automatically using or proposing one of a method based on Baysean statistics and a method based on deep learning when the reliability of the modified CT volume image is smaller than the pre-determined threshold value, the first image enhancement type used by the image enhancement method being the other of the method based on Baysean statistics and the method based on deep learning.

10. In a non-transitory computer-readable storage medium that stores instructions executable by one or more processors to evaluate a reliability of computed tomography (CT) volume images of an examination object, the instructions comprising:
   acquiring a computationally reconstructed first CT volume image from scanned projection images of the examination object;
   acquiring a modified CT volume image of the examination object for image artifact reduction using an image enhancement method, the image enhancement method using a first image enhancement type;
   determining at least one projection direction for which a simulated radiation beam penetrates at least one voxel of the modified CT volume image, the at least one voxel being modified in comparison with the computationally reconstructed first CT volume image;
   calculating, for the at least one determined projection direction, at least one digitally reconstructed X-ray image, respectively, from the computationally reconstructed first CT volume image and from the modified CT volume image;
   determining a similarity, in each case, between the at least one digitally reconstructed X-ray image calculated from the computationally reconstructed first CT volume image and the respective corresponding scanned projection image, and between the at least one digitally reconstructed X-ray image calculated from the modified CT volume image and the respective corresponding scanned projection image;
   comparing, for evaluating the reliability of the CT volume images, the determined similarities with one another; and
   automatically using or proposing a method for image optimization different than the image enhancement method when the reliability of the modified CT volume image is smaller than a pre-determined threshold value, the method for image optimization using a second image enhancement type, the second image enhancement type being different than the first image enhancement type.

11. The non-transitory computer-readable storage medium of claim 10, wherein the computationally reconstructed first CT volume image is already reconstructed as a CT volume image adapted through estimates based on prior knowledge for an improved image quality, and the modified CT volume image is generated by local modifications from the computationally reconstructed first CT volume image.

12. The non-transitory computer-readable storage medium of claim 10, wherein acquiring the computationally reconstructed first CT volume image comprises reconstructing the computationally reconstructed first CT volume image using only information contained directly in the scanned projection images and no estimates extending therebeyond, and
   wherein acquiring the modified CT volume image comprises generating the modified CT volume image using the estimates.

13. The non-transitory computer-readable storage medium of claim 10, wherein the determined similarities are characterized by a likelihood function,
   wherein the instructions further comprise calculating, for evaluation of the reliability using the likelihood function, in each case, a likelihood for the computationally reconstructed first CT volume and a likelihood for the modified CT volume, and
   wherein the likelihood for a CT volume image is a maximum when a digitally reconstructed X-ray image calculated therefrom and the corresponding scanned projection image are identical.

14. The non-transitory computer-readable storage medium of claim 13, wherein the instructions further comprise:
   determining a noise of the scanned projection image; and
   evaluating the reliability depending on whether a difference between the likelihood calculated for the computationally reconstructed first CT volume image and the likelihood calculated for the modified CT volume image is larger or smaller than the determined noise.

15. The non-transitory computer-readable storage medium of claim 10, wherein the instructions further comprise generating, for the modified CT volume image, the computationally reconstructed first CT volume image, or the modified CT volume image and the computationally reconstructed first CT volume image, a confidence map that shows at least for each voxel modified by the image enhancement method, a corresponding reliability.

16. The non-transitory computer-readable storage medium of claim 15, wherein the reliabilities entered in the confidence map are color-coded according to a pre-defined scheme depending upon sizes.

17. The non-transitory computer-readable storage medium of claim 10, wherein the instructions further comprise automatically issuing an indication to a user when the reliability is smaller than a pre-determined threshold value.

18. A system for evaluating a reliability of computed tomography (CT) volume images of an examination object, the system comprising:
   an acquisition device configured to acquire a computationally reconstructed first CT volume image from scanned projection images of the examination object; and
   a data processing device connected to the acquisition device, the data processing device comprising a non-transitory computer-readable storage medium and one or more processors, the non-transitory computer-readable storage medium storing instructions executable by the one or more processors to:
   acquire a computationally reconstructed first CT volume image from scanned projection images of the examination object;
   acquire a modified CT volume image of the examination object for image artifact reduction using an image enhancement method, the image enhancement method using a first image enhancement type;
   determine at least one projection direction for which a simulated radiation beam penetrates at least one voxel of the modified CT volume image, the at least one voxel being modified in comparison with the computationally reconstructed first CT volume image;

calculate, for the at least one determined projection direction, at least one digitally reconstructed X-ray image, respectively, from the computationally reconstructed first CT volume image and from the modified CT volume image;

determine a similarity, in each case, between the at least one digitally reconstructed X-ray image calculated from the computationally reconstructed first CT volume image and the respective corresponding scanned projection image, and between the at least one digitally reconstructed X-ray image calculated from the modified CT volume image and the respective corresponding scanned projection image;

compare, for evaluation of the reliability of the CT volume images, the determined similarities with one another; and automatically use or propose a method for image optimization different than the image enhancement method when the reliability of the modified CT volume image is smaller than a pre-determined threshold value, the method for image optimization using a second image enhancement type, the second image enhancement type being different than the first image enhancement type.

\* \* \* \* \*